United States Patent [19]

Larsen

[11] Patent Number: 5,741,525
[45] Date of Patent: Apr. 21, 1998

[54] VAGINAL PHARMACEUTICAL HYDROGEN PEROXIDE COMPOSITION

[75] Inventor: Bryan Larsen, Huntington, W. Va.

[73] Assignee: Marshall University Research Corporation, Huntington, W. Va.

[21] Appl. No.: 547,518

[22] Filed: Oct. 24, 1995

[51] Int. Cl.$^6$ ............................................. A61K 33/40
[52] U.S. Cl. .......................... 424/616; 424/407; 424/613; 424/430; 424/434; 424/436; 514/714; 514/718
[58] Field of Search ........................... 424/613, 616, 424/434, 436, 407, 430; 514/718, 714

[56] References Cited

U.S. PATENT DOCUMENTS

| | | | |
|---|---|---|---|
| 4,226,848 | 10/1980 | Nagai et al. | 424/19 |
| 4,781,923 | 11/1988 | Pellico | 424/130 |
| 5,008,106 | 4/1991 | Merianos et al. | 424/80 |
| 5,296,239 | 3/1994 | Colery et al. | 424/613 |
| 5,466,463 | 11/1995 | Ford | 424/433 |
| 5,472,704 | 12/1995 | Santus et al. | 424/435 |

OTHER PUBLICATIONS

WPIDS Abstract, AN 93-369193 [47] (Vilaca) BR 9200689, 1993.

*Primary Examiner*—Marianne M. Cintins
*Assistant Examiner*—M. Moezie
*Attorney, Agent, or Firm*—Gary M. Nath; Todd L. Juneau; Nath & Associates

[57] ABSTRACT

Gelled vaginal pharmaceutical composition containing:
a water-soluble bioadhesive polymer, a peroxide source and pH buffer wherein the composition has a pH between about 3.0 and about 6.0; and methods of using same.

4 Claims, 2 Drawing Sheets

5,741,525

VAGINAL PHARMACEUTICAL HYDROGEN PEROXIDE COMPOSITION

BACKGROUND OF THE INVENTION

1. Field of the Invention

The present invention is directed to a vaginal pharmaceutical composition which is in gel form and particularly to a composition which is able to maintain or enhance the normal protective function of the vaginal flora. More particularly, it relates to a vaginal composition useful for the prevention, treatment, mitigation, diagnosis and cure of diseases and the prevention of conception.

2. Description of the Prior Art

One of the main disciplines of medicine is the treatment of the female reproductive system for the prevention, treatment, mitigation, diagnosis and cure of diseases, and the prevention of conception. Usually, this involves the delivery of active agents to the vaginal cavity and its environs. Systems to effect the delivery of such agents are usually in the form of gels, foams, creams, suppositories and quick dissolving tablets.

The vaginal cavity is subject to conditions which render it a target for disease and infection; however, it is extremely difficult to deliver an active agent to this area for an extended period of time. The vaginal cavity exhibits an aqueous environment containing secreting glands whose fluids create an acidic pH in the range of 4.0 to 5.5. The environment of the vagina is conductive to the growth of bacteria, fungi, yeast and other microorganisms since it warm, moist and dark. It is also the vestibule for menstrual debris and residual seminal fluid from sexual intercourse. The crevices of the vaginal cavity facilitate the retention of undesirable bacteria, fungi, yeast and other microorganisms, as well as the debris from menstruation and sexual intercourse. The vaginal cavity is also subject to considerable physical deformation, such as during sexual intercourse or during the insertion of tampons.

Infectious diseases and other inflammatory conditions affecting the vaginal mucosa and often secondarily involving the vulva are commonly referred to as vulvovaginitis. Physicians and investigators often believe that the normal vaginal flora has a role in protecting the vagina and contiguous tissues from various microorganisms that are causes of vulvovaginitis.

Most vulvovaginitis and symptomatic vaginal discharges are caused by bacteria, usually Gardnerella vaginalis in combination with various anaerobes. Protozoa (Trichomonas vaginalis) cause one-third of all cases. Candida is a frequent cause in pregnant women and diabetics, and occasionally oral contraceptives increase susceptibility. Candida also causes symptoms in women who do not have the risk factors of diabetes, pregnancy, and hormonal therapy.

Another major cause is the human papillomavirus (HPV). The lesions from HPV are usually not described as vulvovaginitis although they do cause vulvovaginal infection. The condition is not inflammatory (vaginitis) but rather wart-like outgrowths of the tissue of the vagina, vulva and cervix and usually do not elicit any symptoms of pain or itching. But most importantly HPV is probably the most significant cause of cervical cancer in women.

Other less common causes of vulvovaginitis are other bacteria (e.g., *Neisseria gonorrhoeae*, members of the Chlamydia and Mycoplasma groups, streptococci, *Escherichia coli*, and staphylococci), foreign bodies, viral infections (herpes simplex and HIV infections), pinworms (*Enterobius vermicularis*), fistulas, radiation, and tumors of the genital tract. Frequent douching, especially with chemicals, may disturb normal vaginal milieu. Deodorant sprays, laundry soaps and fabric softeners, and bath water additives may cause vulvar irritation. Tight, nonporous, nonabsorbent underclothing, as well as poor hygiene, may foster fungal and bacterial growth. Occasionally, sensitivity to spermicides, coital lubricants, or latex in a diaphragm or condom causes irritation.

Active agents which have pharmaceutical qualities have been developed and approved for use in the treatment of afflictions of the vaginal cavity and the prevention of conception. These include fungicides, spermicides, etc. Although pharmaceutically active agents have been developed, it has been difficult to achieve optimal potential effectiveness from these agents. It has been found that gels, foams, creams, suppositories and tablets that are presently used as vaginal delivery systems break down almost immediately following insertion into the vaginal cavity and have minimal bioadherence to the vaginal walls. This is believed to be due to their water miscibility and/or their lack of physical stability at 37 degrees C. (body temperature). Thus, they exhibit limited effectiveness.

In this regard, some of the more conventional treatment regimens for various vaginal diseases have been described as follows: Candida is treated topically with miconazole 2% or clotrimazole 1% cream, vaginal tablets, or suppositories for three to seven days. Trichomonas is treated with metronidazole 250 mg rid or 500 mg bid orally for five days; 2 gm in a single daily dose may be used. Ideally, the sexual partner should also be treated. Gardnerella or anaerobic infections are treated similarly to Trichomonas, with metronidazole. About 25% of patients have recurrences and require re-treatment in two to three months. Lowering vaginal pH with propionic acid jelly has also been suggested. Chlamydial infections are treated with doxycycline 100 mg bid or erythromycin 500 mg qid orally for seven days. Mycoplasma is treated with doxycycline 100 mg bid orally for ten days. For any of these infections, sexual partners should be treated simultaneously, if possible.

Conventional treatments thus have two important negative characteristics. Some of the treatments described are systemic, such as oral metronidazole for trichomonas or bacterial vaginosis and tetracycline for chlamydia. Systemic treatment may have systemic side effects. The second difficulty is that while some treatments are listed that are available, for some infectious agents, such as HIV, there is no treatment or preventive product available. This is a serious deficiency in current therapy. Also, Herpes infections are treated with oral, injectable or topical acyclovir which is a nucleoside analog and may induce some unwanted side effects and precautions include issues of carcinogenesis, mutagenesis and impaired fertility.

Furthermore, none of these treatments or procedures, however, attempt to normalize the vaginal flora growth habitat by either maintaining or enhancing acceptable microbial growth patterns.

The present invention is advantageous in that it provides a system for the delivery of an active agent in a controlled manner in the vaginal cavity for an extended period of at least three hours. The system may be used to treat a particular disease state or condition as well as be used on a routine basis to maintain normal vaginal floral activity. This system takes the form of a gel which is easily introduced into the vaginal cavity but does not seep from this body cavity in an offensive manner. It is further advantageous since it reduces the treatment period for active agents including antifungals, such as, imidazoles. It also possesses antimicrobial activity against a variety of microorganisms responsible for sexually transmitted infections and vaginitis acting through direct antimicrobial action and by maintaining and enhancing the normal protective function of the vaginal flora.

SUMMARY OF THE INVENTION

One aspect of the present invention involves the formation of a gelled vaginal pharmaceutical composition, which comprises a water-soluble bioadhesive polymer, a peroxide source and a pH buffer wherein the composition has a pH between about 3.0 and about 6.0.

Another embodiment involves a method for maintaining or enhancing the normal protective function of vaginal flora, which comprises administering a therapeutically effective amount of a gelled vaginal pharmaceutical composition into the vaginal cavity.

A further embodiment involves a method for treating a vaginal infection, which comprises administering to the vaginal cavity a therapeutically effective amount of a vaginal pharmaceutical composition comprising a water-soluble acrylic acid polymer, an active therapeutic agent, a peroxide source and a pH buffer wherein the pH of the composition is between about 3.0 and about 6.0.

An additional embodiment involves a gelled vaginal contraceptive composition which comprises a water soluble polymer, a peroxide source, an active spermicidal agent, and buffer, wherein the composition has a pH between about 3.0 and about 6.0.

DESCRIPTION OF THE PREFERRED EMBODIMENTS

Figure 1:
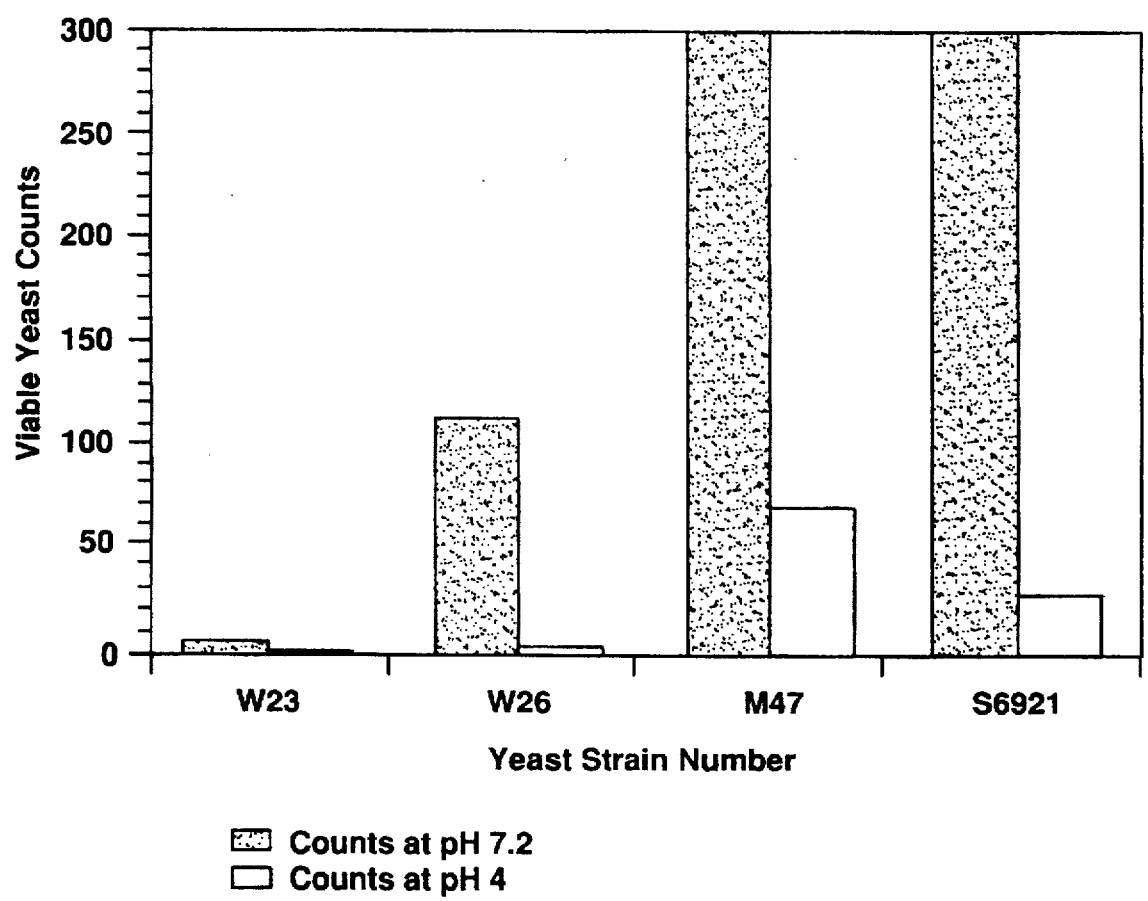
FIG. 1 graphically depicts the antifungal activity of hydrogen peroxide against four yeast strains at various pH levels.

The present invention is directed to vaginal delivery systems. The systems are characterized by their ability to possess antimicrobial action while maintaining and enhancing the normal protective function of vaginal flora.

The presence of vaginal bacteria flora in symptomatic and asymptomatic women has been known for more than a century. At times it has been a mere curiosity, assumed to have little clinical or biological significance. But early on, the dominance of gram positive rods (now known to be Lactobacillus species) was considered to reflect a healthy condition of the vaginal tissue. Further, it was believed that heavy colonization by these benign bacteria was the consequence of estrogen-driven glycogen deposition. The growth of the Lactobacilli and Corynebacteria result in the production of acidic end products which make the vagina inimical to pathogenic organisms. In this regard it should be noted that the vaginal pH is normally between 4.0 to 5.5. It is also known that acidity tends to be decreased by menstrual blood, infected cervical mucus, vaginal transudate or semen.

In the 1960's methods for culture and the identification of anaerobic bacteria became available which led to recognition of the importance of this category of microorganisms in colonized tissues. Concepts of ecology were applied to the normal flora of the gut, emphasizing the importance of the microenvironment, biodiversity of the colonizing organisms and interactions among colonizing species. See Savage DC. *Associations an physiological interactions of indigenous microorganisms and gastrointestinal epithelia.* Am. J. Clin. Nutr. 25:1372–2379, 1972. Following this lead, various investigators began to learn that the vaginal flora of asymptomatic women also consisted of a diversity of species including aerobic and anaerobic bacteria. See Gorbach, S. L., Menda, K. B., Thadepalli, H., Keith, L. *Aerobic and anaerobic flora of the cervix in healthy women.* Am. J. Obstet. Gynecol. 117:1053–1055, 1973, and Galask, R. P., Larsen, B., Ohn, M. J. *Vaginal flora and its role in disease entities.* Clin Obstet Cynecol. 19:61–81, 1976.

As a result, two important concepts were developed. First, the bacteria of the female genital tract are in dynamic equilibrium with the underlying epithelium so that changes in the tissue are reflected in changes in the pattern of colonization, though such changes seem to have limits. Second, a large variety of infectious processes have a profound relationship to alterations in the normal vaginal flora. Thus, many types of vaginitis appear to be endogenous in origin, resulting from an altered distribution of normal flora organisms. Exogenous infections, including sexually transmitted infections interact with the normal vaginal bacterial species.

Currently, the ultimate mechanism for the association of Lactobacilli with absence of vaginal symptoms is unknown. Lactobacilli themselves could produce vaginal salubrity through suppression of other microorganisms, or conversely, conditions extant during vaginal infection may simultaneously suppress or eliminate Lactobacilli resulting in the mere appearance of a protective role for the Lactobacilli. Lactobacilli in the form of yoghurt douches or tableted bacterial inocula have been promoted as alternatives to conventional treatments for vulvovaginitis. Unfortunately, many of the Lactobacillus-based products which have previously been applied as intravaginal therapeutics were adapted for growth in milk products and fail to possess the necessary colonization factors (adhesins, for example) to stably associate with the vaginal epithelium. Viable Lactobacilli could bear a small but definite risk of occasionally causing symptomatic infections in some immunocompromised individuals. Indeed, some researchers suggest that a type of vaginitis they describe as cytolytic vaginosis, is associated with inappropriately increased numbers of Lactobacilli. Others have hypothesized that only the Lactobacilli acquired at birth can colonize the vagina because such strains immunologically tolerize the host. This latter view, while only speculative, suggests that effective colonization by a probiotic Lactobacillus strain would be futile.

It has been unexpectedly discovered that certain Lactobacilli may be associated with production of low concentrations of hydrogen peroxide which aid in moderating cell growth of other microbial species. It is believed that those Lactobacilli which may be hydrogen peroxide producers appear to rely on a flavoprotein system for electron transport, but not all strains produce hydrogen peroxide. However those that do produce hydrogen peroxide tend to be associated with absence of bacterial vaginosis. Information on the precise mechanism whereby hydrogen perioxide exerts this apparently protective effect over bacterial vaginosis is not clear, but it is unlikely acting by eradicating microbial species from the flora. Even in asymptomatic women, the organisms that dominate in bacterial vaginosis (Gardnerella and Bacteroides) are often present, although not numerically dominant suggesting the natural role of Lactobacillus may primarily be regulatory rather than bactericidal.

Not surprisingly, the role of hydrogen peroxide has been extended to other microbial systems. It has been found that Neisseria gonorrhoeae is inhibited by low concentrations of hydrogen peroxide in vitro and hydrogen perioxide producing Lactobacilli can inhibit the Gonococcus as well, but do so only at acidic pH. Hydrogen peroxide may be involved in producing an antimicrobial effect through participation with compounds in addition to hydrogen peroxide. The role of peroxidase-halide and peroxide is well known as an intraphagocytic antimicrobial mechanism, but it may function in vitro or in an extracellular environment as well.

It has been unexpectedly found that hydrogen peroxide, when properly buffered, mimics the natural antimicrobial activity of the vaginal flora and aids in maintaining and enhancing a natural protective function. In the present invention, a product is prepared which incorporates hydrogen peroxide or other peroxide source directly into a gel vehicle. The vehicle is buffered to a low pH which stabilizes the peroxide source and renders it at least more physiologic with regard to pH. Chloride ion can also be present in the preparation in minute concentrations because it may augment the antimicrobial activity of endogenous peroxidase that may contribute not only to protection against bacterial pathogens, but some viral pathogens as well. It should be noted, however, that chloride may cause the gel structure to collapse when using carbopol polymers, even though amounts of added chloride and certainly other gelling agents (not carbopol) could be used if the presence of chloride is critical. However, chloride is present in vaginal secretions and this is probably sufficient without its addition to the carbopol gel. Addition of sodium chloride will also assure isotonicity of the preparation. Finally, the peroxide content must be adjusted to a level which is not profoundly harmful to normal flora.

The peroxide source may be selected from a variety of sources of peroxide, both organic and inorganic. Acceptable forms are those routinely used for treating mucosa and related epithetial tissue, and particularly those used in dental bleaching applications. A preferred source of peroxide is hydrogen peroxide. The peroxide source functions as an oxidizing agent and thus serves as a strong antimicrobial agent. In addition, it has been found that when used in limited concentrations it functions along with endogenous peroxidase and chloride which aid in bacterial or fungal membrane or viral envelope destruction. It has been noted that only selective microbial cell destruction is encountered when low concentrations of peroxide are used to supplement the normal peroxide present in the vaginal cavity.

As indicated the peroxide source is used in amounts that enable vaginal floral activity to be maintained or enhanced without destruction of naturally occurring Lactobacillus and small levels of other microbial and fungal cell activity. Acceptable amounts have been found to range from about 0.1% to about 3.0% with preferred amounts being between about 0.3% and about 1.0%.

Amounts below about 0.1% have been found to be unsuitable to have any meaningful inhibitory effect on a wide variety of microorganisms. Amounts above about 3.0% have been found to be destructive of the natural microbial balance sought to be maintained or enhanced.

The vehicle used to deliver the peroxide source may be selected from a variety of materials which are water-soluble and preferably bioadhesive. The materials must be non-toxic and contain non-carcinogenic byproducts. It is also desirable to employ materials that are not petrolatum based which are incompatible with latex compounds used in condoms.

Particularly preferred vehicles include acrylic acid polymers including polymers modified by long chain ($C_{10}$–$C_{30}$) alkyl acrylates. A representative vehicle is manufactured by B. F. Goodrich and is identified as a carbopol polymer having viscosities of around 29,400–39,400. Useful vehicles should also possess a pH around 3 to 6 to be compatible with the normal vaginal pH of 4.0 to 5.5 and furthermore be stable when pH buffers in the range of vaginal pH are used.

It has been unexpectedly discovered that carbopol polymers prepared from acrylic acid tend to repel microorganisms which would adhere to vaginal epithelial cells. This compound thus also aids in inhibiting adhesion of microbial cells to the vaginal wall. This is quite surprising and would assist in eliminating the transmission of HIV-infected cells during intercourse.

Carbopol is a solid polymeric resin which must be absorbed or suspended in a liquid medium to prepare the translucent gels used in the present compositions. Suitable suspending media include water, glycerin and propylene glycol with aqueous glycerin solutions being preferred.

The polymer is present in amounts that prepare a stable gel preparation. Amounts of about 1.0% to about 3.0% have been found acceptable for this purpose with preferred amounts being about 1.5% to about 2.5%.

The preparations of this invention must possess a pH between about 3.0 to about 6.0 and preferably between about 3.4 and 5.5. pH's below 3.0 are not recommended in view of the potential to cause epithelial cell damage. pH's above 6.0 are not preferred since they promote vaginal infections and inflammation. When necessary, buffers are used to adjust the pH of the system. Acceptable buffers are those that do not render the peroxide source unstable and include commonly used mixtures of a weak acid and its conjugate base, such as acetic acid and sodium acetate. Acceptable buffers may be based on inorganic salts such as phosphate and carbonate, and organic acid sodium and potassium salts such as acetate, citrate, succinate, formate, glycine, maleate and barbiturates, with sodium citrate being preferred.

It has also been unexpectedly found that the microbial kill rate due to hydrogen peroxide for undesirable microbes is 20 to 50 times more effective at pH's around 4.0.

The gelled compositions of this invention are formed by preparing a translucent gel of the polymer in a suitable carrier. One procedure would involve mixing the acrylic acid polymer with glycerine until the polymer is completely absorbed by the glycerine. Acceptable amounts of polymer to glycerine for this purpose may range from a ratio of 1:5 to 20 w/w. The peroxide source along with the pH buffer may then be added to the vehicle followed by the optional addition of other excipients or additives. It should be recognized that other processes may be used to prepare the composition of this invention depending on the vehicle being used to prepare the gel composition and excipients employed.

As discussed above, the compositions may contain an additional therapeutic active agent as well as a spermicide. The additional active agent may be any of those which are approved for or used for the treatment, prophylaxis, cure or mitigation of any disease of the vulva, vagina, urinary tract, cervix or other female reproductive organ or preventant of conception; for aesthetic or cosmetic usage, for diagnostic purposes; for systemic drug therapy; or for sex determination of offspring. The agent must have utility when administered by delivery to all or a portion of the vaginal surfaces. Therapeutic active agents are normally well-known due to their need for governmental approval or common usage. Without being limited thereto, exemplary agents include:

antibacterial agents such as C31G, trimethoprim, sulfamethoxazole, and chloromycetin;

antiseptic agents such as chlorhexidine gluconate;

antibiotic agents such as erythromycin, penicillins, cephalosporins and their derivatives, ampicillin, methicillin, and doxycycline;

anti-inflammatory agents such as naproxen, indomethacin, and hydrocortisone;

antiparasitic agents such as thiabendazole;

antiprotozoal agents such as metronidazole, and chloroquine hydrochloride;

antiviral agents such as dextran sulfate and other sulfated polysaccharides, n-Docosanol (Lidak Pharmaceuticals), squalamine, and vidarabine;

and antifungal agents such as ketoconazole, flucytosine, itraconazole, amphotericin B, nystatin, butoconazole nitrate, and clotrimazole.

In addition to the active therapeutic agent it may also be desirable to add a chloride salt, to aid in cell membrane lysis. Suitable chloride salts include sodium chloride, potassium chloride, and such other forms of salts as would be stable in the formulations of this invention.

Furthermore, conventional and well known pharmaceutical excipients may be used including emulsifiers, suspending agents, osmotic enhancers, fragrances, preservatives, colors and flavors.

The systems can be introduced into the vaginal cavity by the use of conventional applicators such as tampon injectables or other coating or impregnating means. Although the compositions are deformable at physiological temperatures, approximately 37 degrees C., they do not lose their integrity as do the systems of the prior art. These delivery systems, unlike other systems, are not characterized by offensive leakage from the vaginal cavity following the insertion of the pharmaceutical composition. The volume administered will be from about 2 to 5 milliliters. Greater amounts may cause leakage and lesser amounts may not be effective to provide therapeutic levels of materials.

The compositions release the active agent in the vaginal cavity due to diffusion of the active agent, rupture of unit cells formed by the polymer and/or a combination of these two mechanisms. This release of active agent can be linear or non-linear depending on the ultimate composition. Factors which effect the release rate are the components percentage of active agent; pH of the composition; diffusibility of the active species, etc. Within the physiological environment of the vaginal cavity all of the chemical and physical forces present, including fluids, enzymes, pH, chemical balance, temperature, and shear forces from body movement, affect the rate of breakdown of the composition.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLE 1

This example demonstrates the preparation of a composition containing 0.3% hydrogen in a colorless gel. A pH buffer is prepared by dissolving sufficient sodium citrate in purified water to produce a 0.143 M solution. A 0.143 M solution of citric acid in purified water is also prepared. The aqueous citric acid is added to the sodium citrate solution with constant stirring and pH monitoring until a pH of 5.0 is attained. Hydrogen peroxide (3% USP) is added to the citrate buffer to yield a final concentration of 0.43% hydrogen peroxide (v/v).

In a glass vessel, Carbopol 974P NF is slowly added to glycerine (USP) in a ratio of 1:14 w/w with gentle stirring. When the carbopol has been completely absorbed by the glycerine, the hydrogen peroxide-containing buffer 7 parts buffer to 3 parts of carbopol-glycerine) is added slowly with continuous gentle mixing. Mixing should occur at no more than 50 rpm and should not last longer than two hours. The resulting product is a colorless gel.

EXAMPLE 2

This example demonstrates the preparation of a pharmaceutical composition containing 0.3% hydrogen peroxide and 1% nonoxynol-9 in a colorless gel. The hydrogen peroxide containing buffer is prepared as described in Example 1. Nonoxynol-9 (USP) is added to glycerine in a ratio of 1:27 (w/w) with constant stirring for 20 minutes at 50 rpm. Carbopol 974P NJ is slowly added to glycerine (USP) in a ratio of 1:14 w/w with gentle stirring. When the Carbopol had been completely absorbed by the glycerine, the hydrogen peroxide-containing buffer (7 parts buffer to 3 parts of Carbopol-glycerine) is added slowly with continuous gentle mixing. Mixing should occur at no more than 50 rpm and should not last longer than 2 hours. The resulting product is a colorless gel.

EXAMPLE 3

A pharmaceutical composition containing 0.3% hydrogen peroxide and 0.01 M sodium chloride in a colorless gel is prepared as follows. A buffer is prepared by dissolving sufficient sodium citrate in a 0.0143 M solution of sodium chloride in purified water to produce a 0.0143 M solution. A 0.143 M solution of citric acid in 0.143 M aqueous sodium chloride is also prepared. The aqueous citric acid is added to the sodium citrate solution with constant stirring and pH monitoring until a pH of 5.0 is attained. Hydrogen peroxide (3% USP) is added to the citrate buffer to yield a final concentration of 0.43% hydrogen peroxide (v/v). A 2% carbopol gel is produced by the same method described in Example 1 by combining the chloride buffer with the Carbopol-glycerine mixture.

EXAMPLE 4

A pharmaceutical composition containing 0.3% hydrogen peroxide, 0.01 M sodium chloride and 1% nonoxynol-9 is prepared as a colorless gel as follows. A chloride and peroxide containing buffer is prepared as described in Example 3. Seven parts of this buffer are mixed with 3 parts of a glycerine-nonoxynol-9-carbopol mixture as described in Example 2 above.

EXAMPLE 5

Candida albicans in vitro test

It was observed that Candida albicans produces catalase activity consistently. This was observed by the generation of bubbles of oxygen when a colony is placed in a drop of 3% hydrogen peroxide solution. This characteristic was noted for 40 Candida strains. Dilutions of hydrogen peroxide were made in PBS or Sabourauds dextrose broth and the dilutions were inoculated with $10^4$ viable yeast and plate counts were performed. Despite the fact that this organism possesses catalase, it was susceptible to hydrogen peroxide. As anticipated, the antimicrobial effect was attenuated in the growth medium compared to the PBS, but an antimicrobial effect was detected under both conditions at a peroxide concentration of 3.4 mM.

The MIC (hydrogen peroxide concentration in Sabouraud's broth that prevents development of turbidity in 24 hours) for yeast isolates was determined. In addition, the catalase activity of whole cells added to a hydrogen peroxide solution was determined (change in absorbance at 240 nm of a 17 mM solution of hydrogen peroxide at room temperature). As illustrated by the table, the susceptibility of Candida to hydrogen peroxide was not a function of the catalase activity of the washed suspension of yeast cells. For the 10 strains that had MIC values of 88 μM (at 3% hydrogen peroxide) the average catalase activity associated with whole cells was 0.0104 ±0.0146 (standard deviation) and the 17 strains that had MIC's of 17 μM had similar catalase activity (mean 0.0103 ±0.0049 sd). It appears that the majority of catalase activity was located intracellularly and was therefore unavailable to degrade the extracellular hydrogen peroxide. In addition, it appeared that very little extracellular catalase activity was present.

The results indicate that all catalase-producing Candida strains were susceptible to hydrogen peroxide concentrations of 88 mM or less in the presence of complex media.

The ability of iron compounds, particularly hemoglobin, to act as a pseudo-catalase was of concern since hemoglobin is periodically present in the vaginal microenvironment, most notably during menstruation. Candida albicans grown in ferric ammonium sulfate (100 uM final concentration), washed, diluted and placed into an MiC experiment did not show decreased susceptibility to hydrogen peroxide. However, when hemoglobin was added directly to the MIC setup, hemoglobin concentrations above 1% did change the endpoint. Consequently, it is unlikely that vaginal therapeutics based on hydrogen peroxide would have any direct efficacy during menses or alternatively a higher concentration or more frequent dosing of the agent may result in the desired effect.

EXAMPLE 6

To predict how vaginal pH might affect hydrogen peroxide, we compared the antifungal activity of hydrogen peroxide against 4 strains of yeast at pH 4 and pH 7.2 We selected 2 yeast strains which had been shown to be quite sensitive to hydrogen peroxide and two which were less sensitive. For this study, we used PBS at pH 7.2 and PBS with pH adjusted to 4.0. To these were added hydrogen peroxide in a final concentration of 44 mM/L for the least sensitive strains (strains W23 and W26) and 2.2 mM/L for the most sensitive strains (strains M47 and S6921). Each tube was inoculated with $1 \times 10^4$ viable yeast cells and incubated for 24 hours at 37° C. Ten ul were plated and the viable counts are presented in FIG. 1 which indicates that the antifungal effect of hydrogen peroxide at pH 4 was greater than at pH 7.2.

EXAMPLE 7

Figure 2:
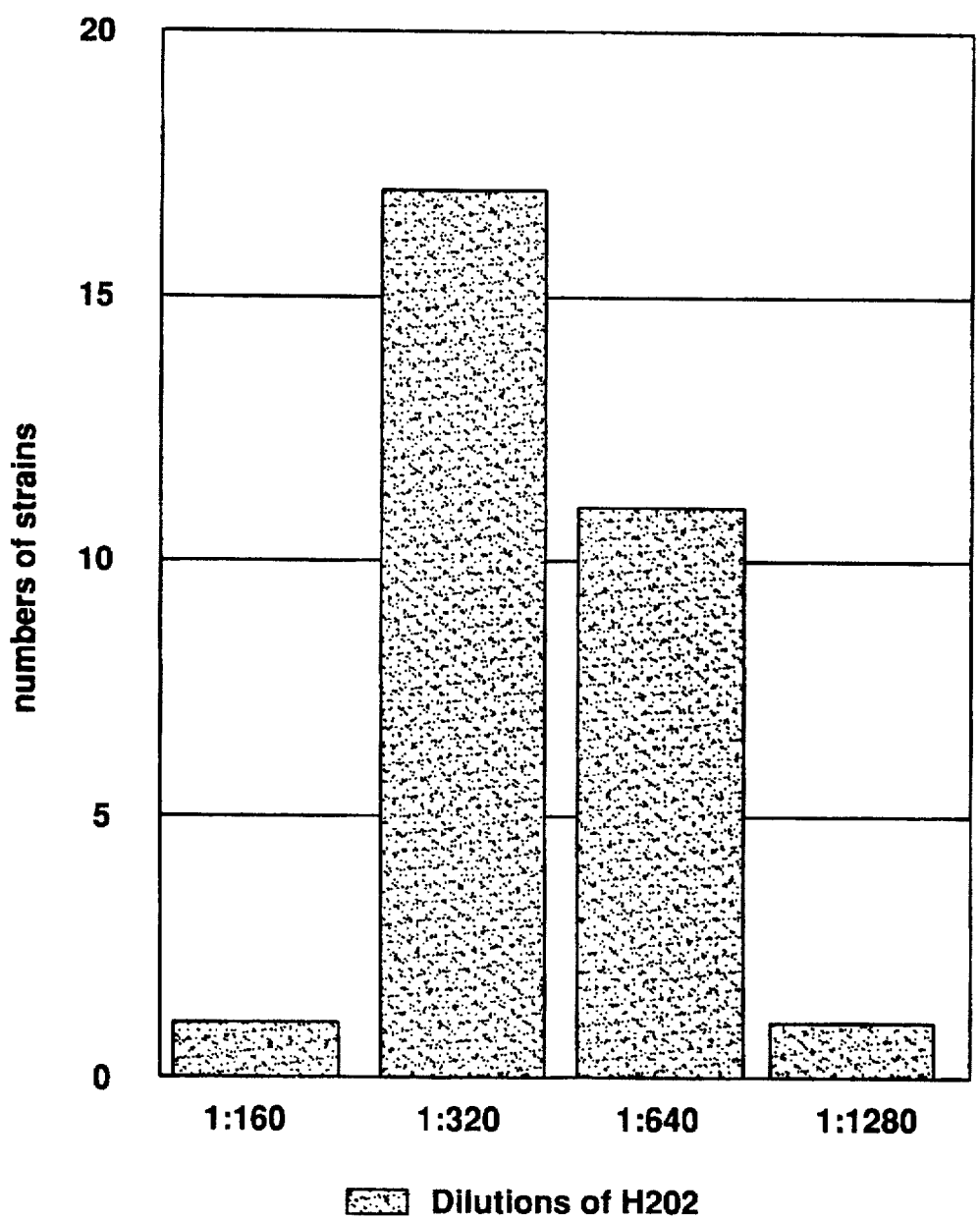
FIG. 2 graphically depicts the MIC of hydrogen peroxide against Group B Streptococcus.

In this example, Group B Streptococcus were tested with various concentrations of hydrogen peroxide. The results are set forth in FIG. 2 and show that this organism (isolated from pregnant women) was susceptible to hydrogen peroxide at dilutions of up to 1:1280 (this is the dilution of 3% USP solution of hydrogen peroxide). It should be noted that this microorganism is the leading cause of bacterial infection and death in infants. This organism is acquired from the mother's birth canal.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method for maintaining or enhancing the normal protective function of vaginal flora, which comprises:

administering a therapeutically effective amount of a gelled vaginal pharmaceutical composition consisting essentially of a pharmaceutically acceptable excipient for use in the vaginal cavity area, a water-soluble bioadhesive acrylic acid polymer which repels microorganisms that adhere to vaginal epithelial cells, an active therapeutic agent, hydrogen peroxide in an amount of about 0.1% to about 3.0% and a pH buffer, wherein the pH of the composition is between about 3.0 and about 6.0 to the vaginal cavity.

2. A method for treating a vaginal infection, which comprises:

administering to the vaginal cavity a therapeutically effective amount of a vaginal pharmaceutical composition consisting essentially of a pharmaceutically acceptable excipient for use in the vaginal cavity area, a water-soluble bioadhesive acrylic acid polymer which repels microorganisms that adhere to vaginal epithelial cells, an active therapeutic agent, hydrogen peroxide in an amount of about 0.1% to about 3.0%, and a pH buffer, wherein the pH of the composition is between about 3.0 and about 6.0.

3. The method of claim 2, wherein the composition has a pH between about 3.4 and 5.5.

4. The method of claim 2, wherein the active therapeutic agent is selected from the group consisting of antibacterial agent, antiseptic agent, antibiotic agent, anti-inflammatory agent, antiparasitic agent, antiprotozoal agent, antiviral agent, antifungal agent and mixtures thereof.

* * * * *